(12) United States Patent
Saitoh et al.

(10) Patent No.: US 8,402,810 B2
(45) Date of Patent: Mar. 26, 2013

(54) METHOD AND APPARATUS FOR TESTING WATER HAMMER STRENGTH OF GLASS BOTTLE

(75) Inventors: Shinji Saitoh, Tokyo (JP); Yuuichi Ohya, Kanagawa (JP)

(73) Assignee: Toyo Glass Co., Ltd., Tokyo (JP)

( * ) Notice: Subject to any disclaimer, the term of this patent is extended or adjusted under 35 U.S.C. 154(b) by 525 days.

(21) Appl. No.: 12/591,481

(22) Filed: Nov. 20, 2009

(65) Prior Publication Data

US 2011/0120210 A1 May 26, 2011

(51) Int. Cl.
*G01N 3/00* (2006.01)
(52) U.S. Cl. ...................................... 73/12.06
(58) Field of Classification Search ............... 73/12.06
See application file for complete search history.

(56) References Cited

U.S. PATENT DOCUMENTS 2,137,984 A * 11/1938 Rumore ..................... 248/141

FOREIGN PATENT DOCUMENTS

| JP | 51-129283 | 11/1976 |
| JP | 59-120934 | 7/1984 |
| JP | 60-171432 | 9/1985 |
| JP | 61-147129 | 9/1986 |
| JP | 62-263435 | 11/1987 |
| JP | 8-145837 | 6/1996 |
| JP | 11-105866 | 4/1999 |

OTHER PUBLICATIONS

Japanese Notice of Allowance dated Apr. 26, 2010 in JP 2007-309733 (including English translation).

* cited by examiner

*Primary Examiner* — Lisa Caputo
*Assistant Examiner* — Octavia Davis-Hollington
(74) *Attorney, Agent, or Firm* — Wenderoth, Lind & Ponack, L.L.P.

(57) ABSTRACT

The present invention provides a method for testing the water hammer strength of a glass bottle. The method includes the steps of providing a holding device on a fixing stage with a cushion material therebetween, holding the bottle filled with a content and fitted with a cap with the holding device at a position above the center of gravity thereof and suspending the bottle in the air, and dropping a weight directly or indirectly onto the cap to apply an impact to the bottle. The weight is repeatedly dropped while gradually increasing a drop energy thereof. The water hammer strength of the bottle is tested based on the drop energy of the weight at the time when the bottle is damaged.

17 Claims, 11 Drawing Sheets

METHOD AND APPARATUS FOR TESTING WATER HAMMER STRENGTH OF GLASS BOTTLE

BACKGROUND OF THE INVENTION

1. Field of the Invention

The present invention relates to a method and apparatus for testing the water hammer strength of glass bottles using a single glass bottle.

2. Description of the Related Art

Figure 11:
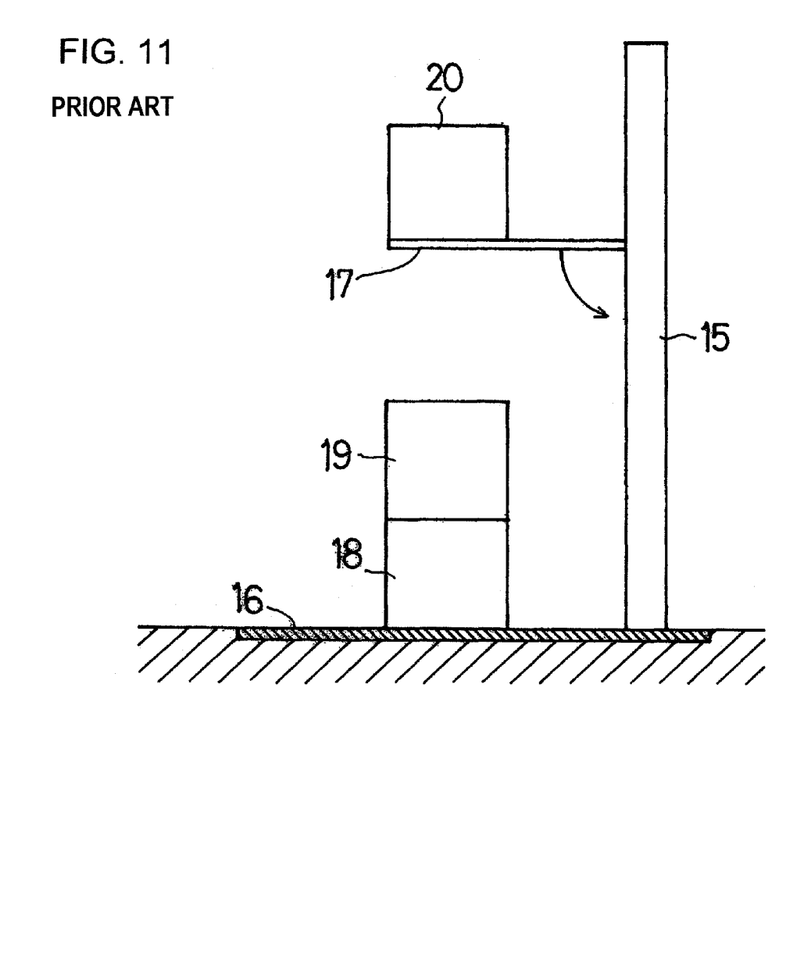
FIG. 11 shows a test method for packaged items.

The water-hammer-strength test of glass bottles is defined by the "water-hammer test method" prescribed by the Japan Glass Bottle Association. This defines the water-hammer test method for glass bottles serving as packaged items. FIG. 11 is a schematic diagram showing the test according to the above-mentioned definition. In this test, a drop testing machine 15 defined by "JIS Z 0202" is used. A case of lower dummies 18 (the same as samples 19) is placed on a drop surface 16 (an iron plate having a thickness of 20 mm or more), and a case of the samples 19 is disposed thereon. A case of upper dummies 20 (the same as the samples) is placed on a sample stage 17 of the drop testing machine 15. The lower dummies 18, the samples 19, and the upper dummies 20 are bottles filled with a predetermined amount of formal content by a formal filling method and fitted with predetermined caps, or other equivalents, that are packaged in a predetermined manner. The cases hold many glass bottles. The sample stage is set to a predetermined drop height (the distance between the bottom surfaces of the upper dummies 20 and the top surfaces of the samples 19). For example, at first, the upper dummies 20 are dropped onto the samples 19 from a drop height of 30 cm. Then, the drop height is increased by an increment of 5 cm (when the drop height is 60 cm or more, the drop height is increased by an increment of 10 cm) to test whether or not the sample glass bottles, even one of them, are damaged. The drop tests are repeatedly performed up to a predetermined drop height, and the drop height at the time when the sample bottles, even one of them, are damaged is regarded as the water hammer strength.

When the upper dummies 20 are dropped onto the samples 19, the case of the lower dummies 18 is deformed, and the glass bottles of the samples 19 are rapidly pushed downward. However, the content (liquid) in the glass bottles remains at the original position due to inertia, creating vacuum portions at the bottoms in the bottles. Immediately thereafter, the content rapidly drops onto the bottoms, which are in vacuum, causing a water hammer effect.

Packaged-items drop test apparatuses are also disclosed in Japanese Unexamined Patent Applications Publication Nos. 61-147129 and 62-263435.

The "water-hammer test method" prescribed by Japan Glass Bottle Association is not for testing the water hammer strength of the glass bottles themselves, but for measuring the water hammer strength of packaged glass bottles (the water hammer strength varies depending on the specification of the package). Furthermore, because the test cannot be performed without preparing cartons, the test requires many products (about 10 cases). Thus, the water hammer strength of bottle parisons cannot be evaluated during test production in the design phase. Moreover, the test requires considerable labor for tasks such as lifting the cartons, checking the bottles for damage, cleaning up of the damaged bottles, checking the cartons for damage, etc.

SUMMARY OF THE INVENTION

The present invention has been made to enable measurement of the water hammer strength of glass bottles themselves with relative ease and to enable strength evaluation during test production (design phase of bottle parisons).

The present invention is a method for testing the water hammer strength of a glass bottle. The method includes the steps of providing a holding device on a fixing stage with a cushion material therebetween, holding the bottle filled with a content and fitted with a cap with the holding device at a position above the center of gravity thereof, suspending the bottle in the air, and dropping a weight directly or indirectly onto the cap to apply an impact to the bottle. The weight is repeatedly dropped while gradually increasing a drop energy thereof. The water hammer strength of the bottle is tested based on the drop energy of the weight at the time when the bottle is damaged.

When the weight is directly or indirectly dropped onto the cap, the cushion material is deformed and the bottle is rapidly pushed downward, causing a water hammer effect. When the weight is dropped onto the bottle that is held at a position above the center of gravity thereof and is suspend, the drop energy of the weight efficiently acts on the bottle. Thus, the drop energy of the weight and the impact applied to the bottle are strongly correlated with each other, and the water hammer strength of the bottle can be accurately known based on the drop energy of the weight at the time when the bottle is damaged.

Furthermore, the present invention is an apparatus for testing the water hammer strength of a glass bottle. The apparatus includes a fixing stage, a cushion material placed on the fixing stage, a holding device that is placed on the cushion material and holds the bottle, which is filled with a content and fitted with a cap, at a position above the center of gravity thereof and suspends the bottle in the air, and a weight that is dropped onto the cap to apply an impact to the bottle.

With the apparatus of the present invention, the method for testing the water hammer strength of the present invention can be easily performed.

The apparatus of the present invention may further include a frame that includes a base stage and a post standing upright from the base stage. The fixing stage may be a plate-like member extending from the post toward one side and having a through-hole, and the bottle suspended in the air by the holding device may be inserted into the through-hole.

The fixing stage of the apparatus of the present invention may include a plurality of posts, and the bottle suspended in the air by the holding device may be positioned so as to be surrounded by the posts.

The fixing stage of the apparatus of the present invention may be a tubular member, and the bottle suspended in the air by the holding device may be positioned in the tubular member.

The apparatus of the present invention may further include a protection plate that covers the cap and is in contact with a top surface of the cap at a bottom surface thereof. The weight may be dropped onto the protection plate so that the weight is indirectly dropped onto the cap via the protection plate. This prevents the cap from being damaged by the impact caused by dropping the weight.

In the apparatus of the present invention, the weight may include a shaft and a weight body formed at a lower end of the shaft, and a guide into which the shaft is inserted may be provided so that the weight can vertically move along a predetermined path. This allows the weight to vertically move along a predetermined path and allows the weight to be accurately dropped onto the cap.

With the present invention, because the water hammer strength of glass bottles themselves can be accurately tested and the number of glass bottles used in the test can be small, the water hammer strength of bottle parisons can be evaluated during test production in the design phase. Accordingly, if, as a result of the test, the strength of the test-production bottles turns out to be insufficient, the design of the bottle parisons can be immediately changed. Thus, high-quality bottles can be efficiently designed. Furthermore, the present invention does not require tasks such as lifting the cartons, checking the bottles in the cartons for damage, checking the cartons for damage, or the like. Thus, the test can be performed with relative ease.

DESCRIPTION OF THE PREFERRED EMBODIMENTS

Figure 1:
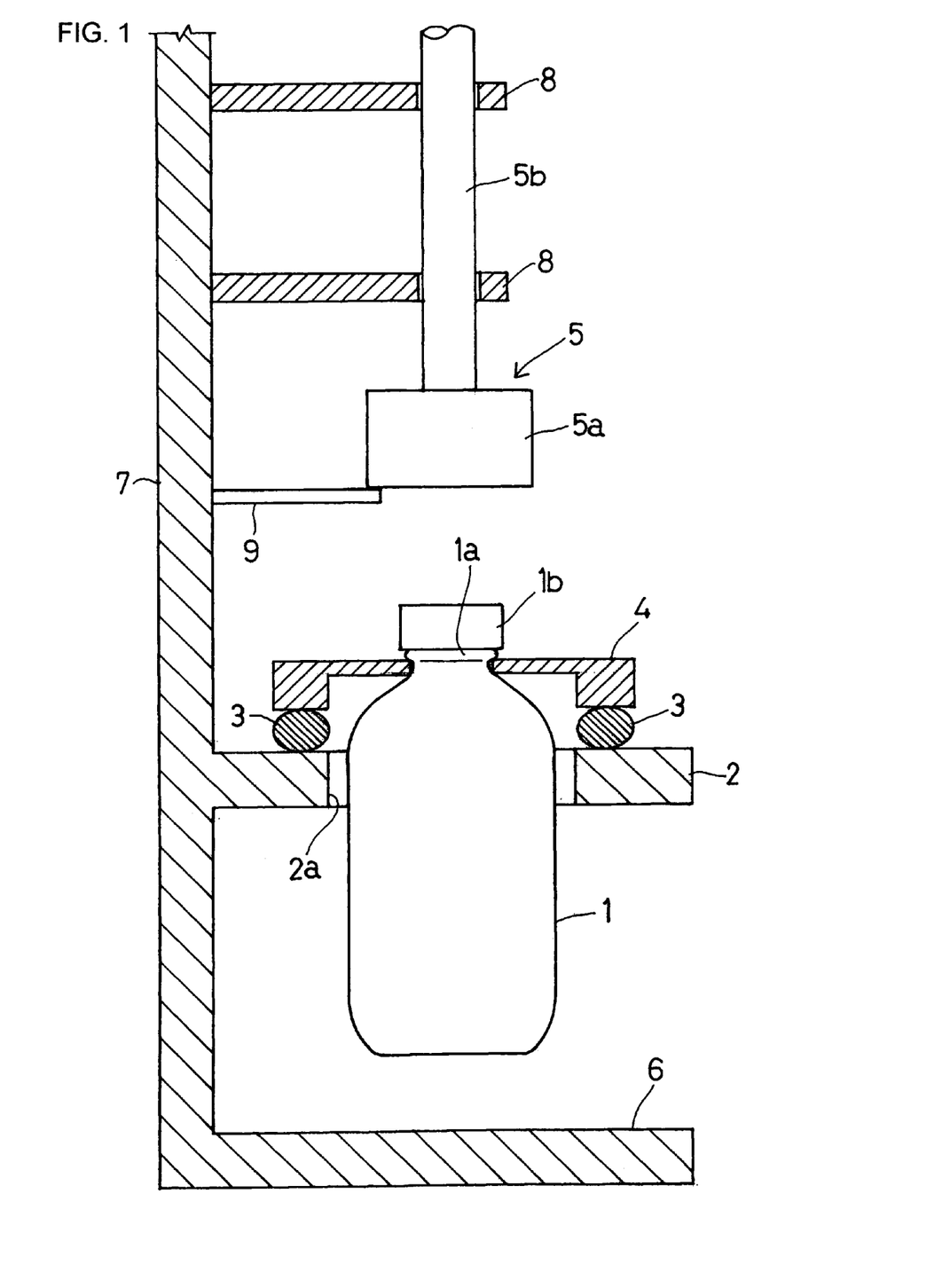
FIG. 1 is a sectional view of a test apparatus according to an embodiment.

FIG. 1 is a sectional view of a test apparatus according to an embodiment. A base stage 6, a post 7, a fixing stage 2 are formed as a single part from a steel plate. The post 7 stands upright from the base stage 6 so as to form an L shape, and the fixing stage 2 projects from the middle of the post 7. The fixing stage 2 has a through-hole 2a into which the body of a bottle 1 can be inserted. A cushion material 3 is disposed on the fixing stage 2, around the through-hole 2a, and a holding device 4 is disposed thereon. The cushion material 3 is made of an elastic material, such as rubber or soft resin, and the shape and size thereof may be selected as necessary. The holding device 4 holds the bottle 1 filled with a content and fitted with a cap at a position above the center of gravity thereof and suspends the bottle 1 in the air. The holding device 4 may be made of any material and may be formed into any shape as long as it can securely hold the bottle 1 and can be placed onto the cushion material 3. Although the bottle 1 filled with a content and fitted with the cap may be held at a position above the center of gravity thereof, it is most desirable that the bottle 1 be held at the neck (immediately below the mouth or the bead).

A weight 5 is provided above a cap 1b of the bottle 1. The weight 5 includes a shaft 5b and a weight body 5a attached to the lower end of the shaft 5b. The weight 5 is vertically moveable by guides 8 projecting from the post 7 and having insertion holes into which the shaft 5a is inserted. The weight 5, held at a desired height by a stopper 9, is dropped right onto the cap 1b by releasing the stopper 9.

When the weight 5 is dropped right onto the cap 1b, the cushion material 3 is deformed by the drop energy and the bottle 1 is rapidly pushed downward, causing a water hammer effect. The weight is repeatedly dropped while gradually increasing the drop energy. Thus, using the drop energy of the weight when the bottle is broken, the water hammer strength of the bottle is measured. The drop energy is adjusted by changing the weight and the drop height (the distance between the bottom surface of the weight and the top surface of the cap or protection plate). The drop energy is mgh, where m is the mass of the weight, h is the drop height, and g is the acceleration of gravity.

Figure 2:
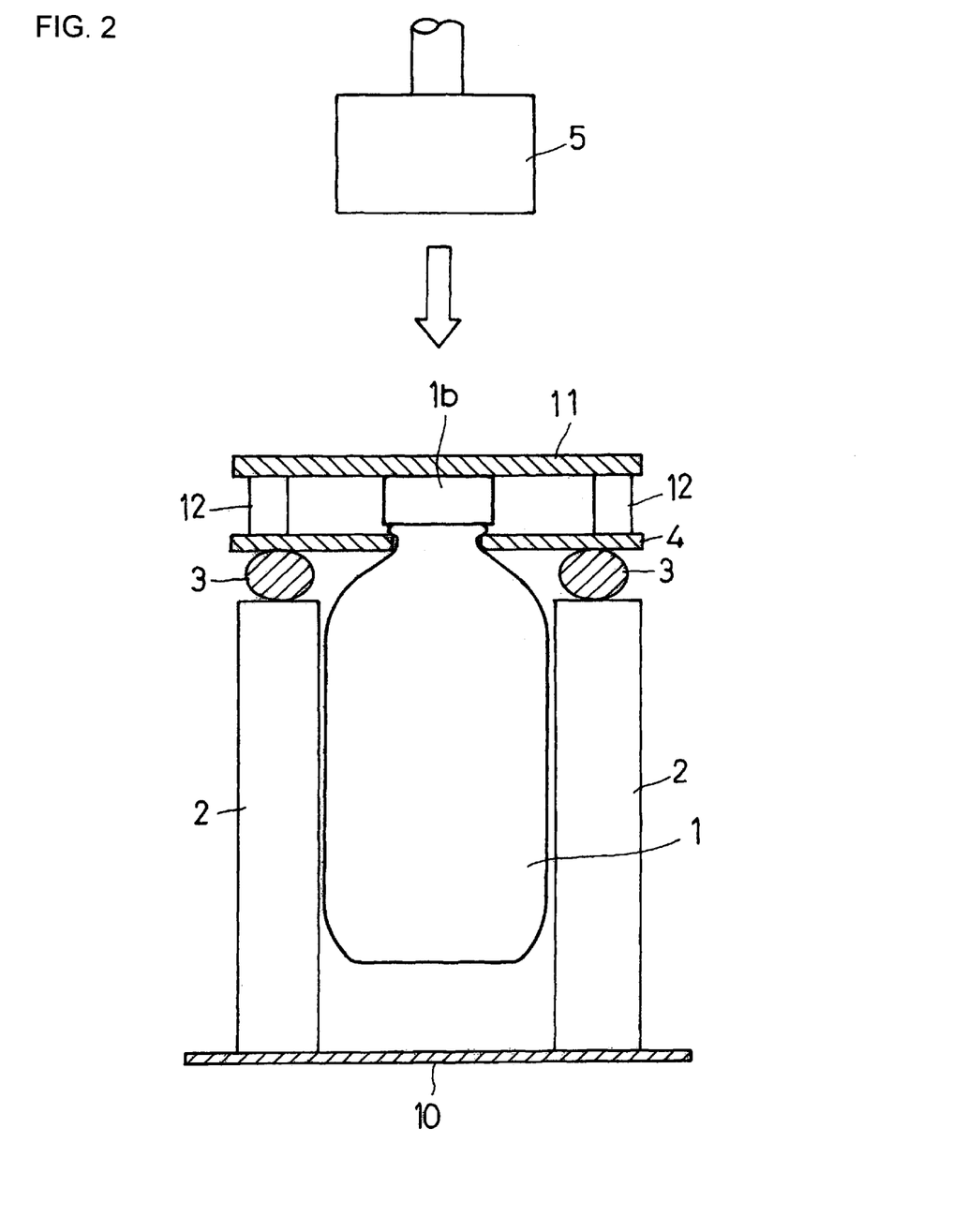
FIG. 2 is a sectional view of a test apparatus according to another embodiment.

FIG. 2 is an example in which the fixing stage 2 includes four posts. The four posts are placed on a bottom plate 10, and the cushion material 3 is disposed on the posts. Then, the holding device 4 for suspending the bottle 1 is placed thereon. The bottle 1 is positioned so as to be surrounded by the four posts. It is also possible that a tubular member, instead of the posts, may be used as the fixing stage 2, and the cushion material 3 and the holding device 4 for suspending the bottle 1 are placed thereon. In such a case, the bottle 1 is positioned in the tubular member. A protection plate 11 covering the cap 1b is provided to prevent the cap 1b from being damaged when the weight is dropped. The top surface of the cap 1b is in contact with the bottom surface of the protection plate 11. Although the weight is dropped onto the protection plate 11, because the top surface of the cap 1b is in contact with the bottom surface of the protection plate 11, an impact equivalent to that caused when the weight is dropped directly onto the cap 1b is applied to the bottle 1. Spacers 12 are provided between the holding device 4 and the protection plate 11. This further prevents the cap 1b from being damaged.

Figure 3A:
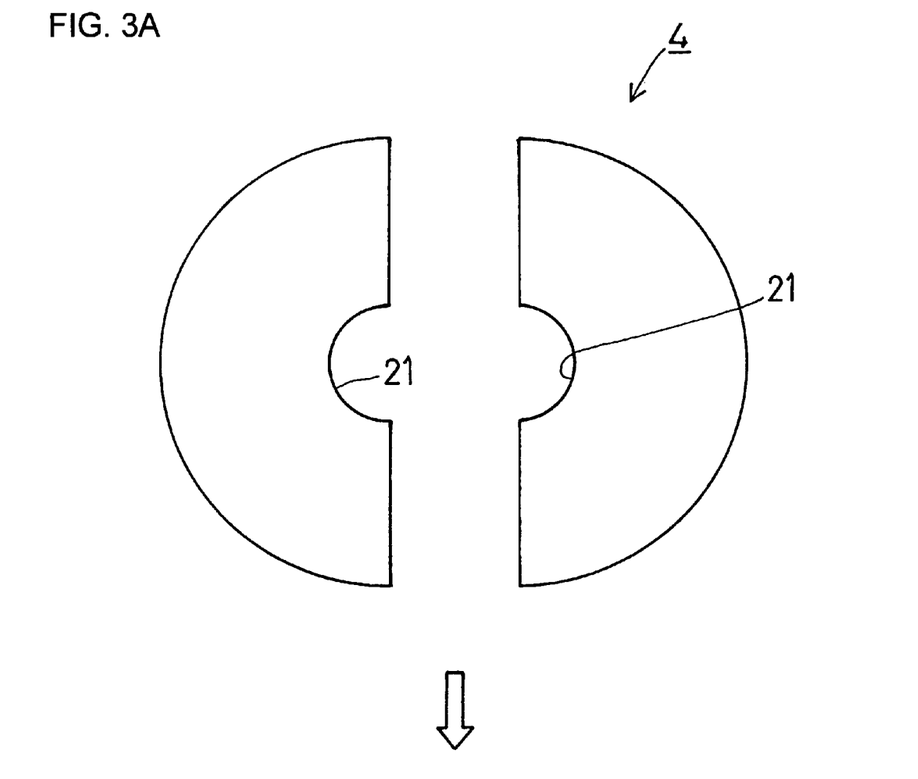
FIGS. 3A and 3B are plan views of an example of a holding device.
Figure 3B:
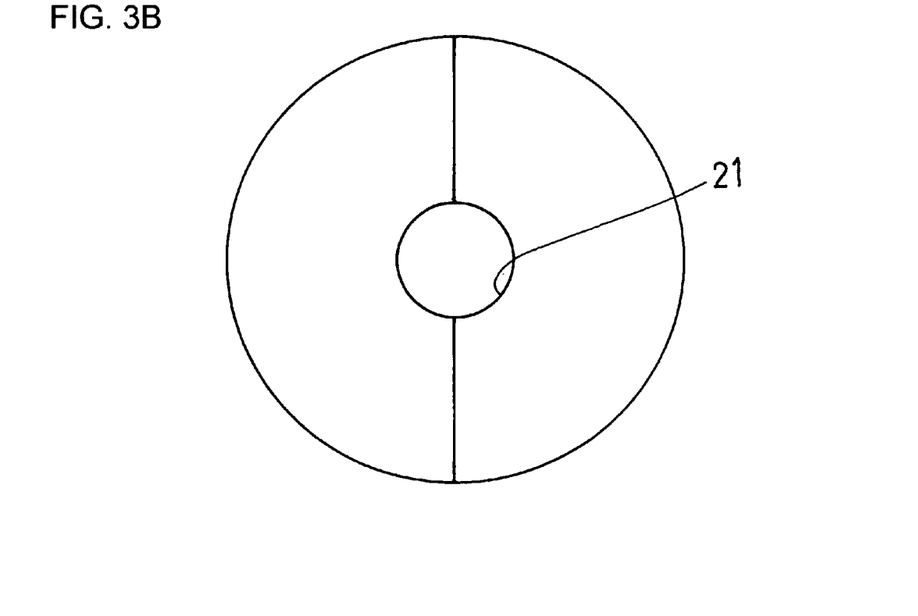
Figure 4A:
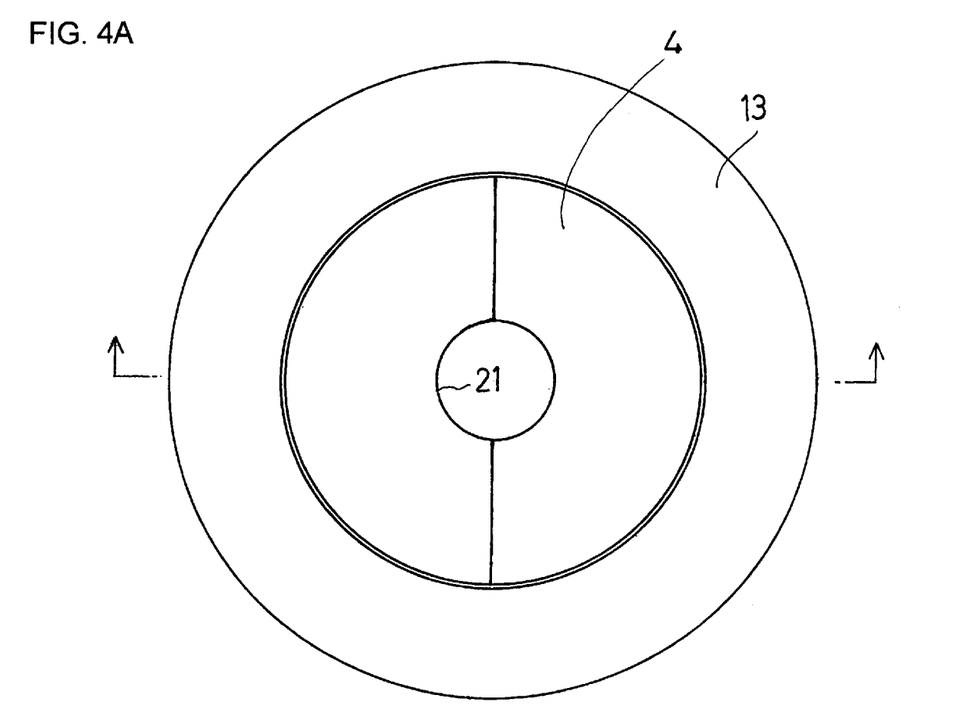
FIGS. 4A and 4B show an example of a fixing device of the holding device.
Figure 4B:
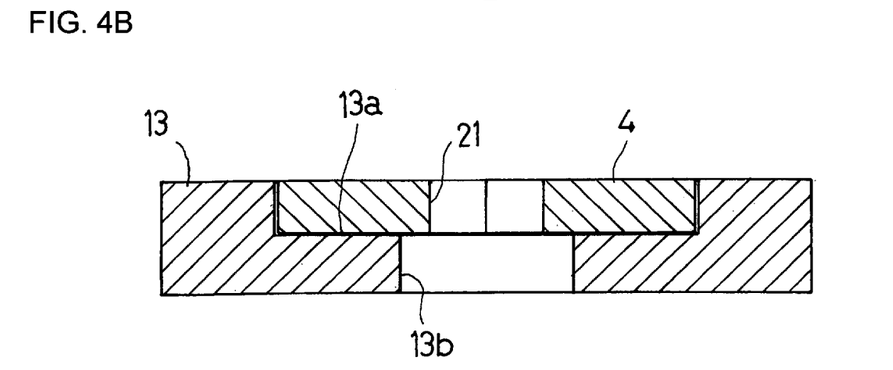

FIGS. 3A and 3B show an example of the holding device 4. In this example, the holding device 4 is a circular plate having an inner hole 21 having the same or a slightly larger diameter than the bottle neck, the circular plate being divided into two at the center thereof. The semicircular parts are fitted together into a single part from both sides such that the bottle neck is fitted into the inner hole 21, as shown in FIG. 3B. Thereafter, desirably, the semicircular parts are fixed by a fixing device so as not to be separated. FIGS. 4A and 4B show an example of the fixing device, showing a plan view and a sectional view, respectively. The fixing device 13 has a plate-like structure and has a recess 13a for receiving the holding device 4 at the center in the top surface. The recess 13a has a hole 13b at the center. The holding device 4 placed in the recess 13a is fixed such that the semicircular parts do not separate. In FIG. 1, the holding device 4 is attached below a bead 1a (circular rib) of the bottle 1. Because the outside diameter of the bead 1a is larger than the inner hole 21 of the holding device, the bottle 1 is securely held by the holding device 4.

Figure 5A:
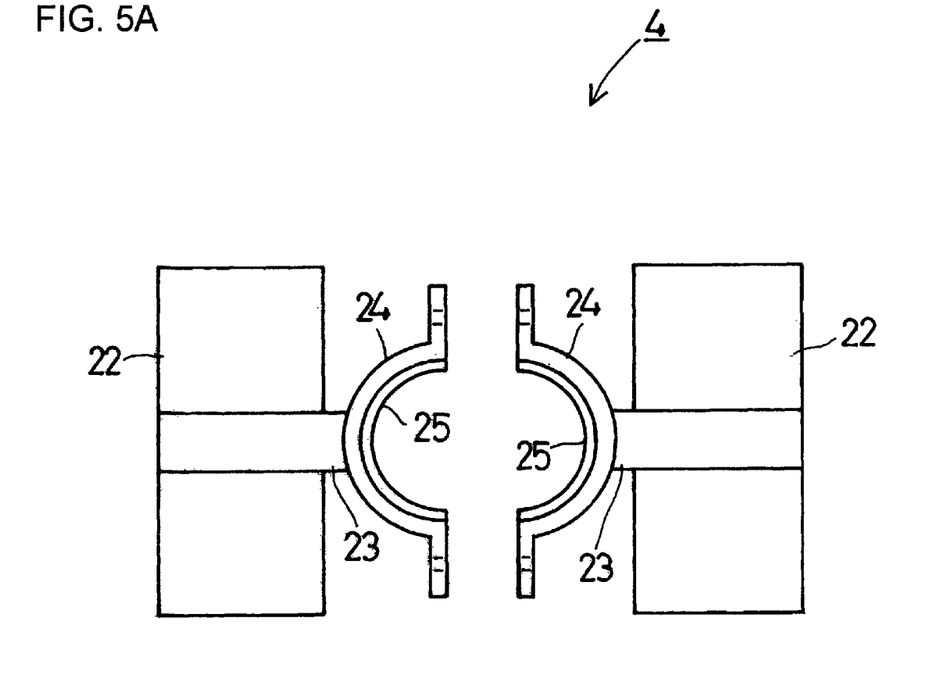
FIGS. 5A and 5B show another example of the holding device.
Figure 5B:
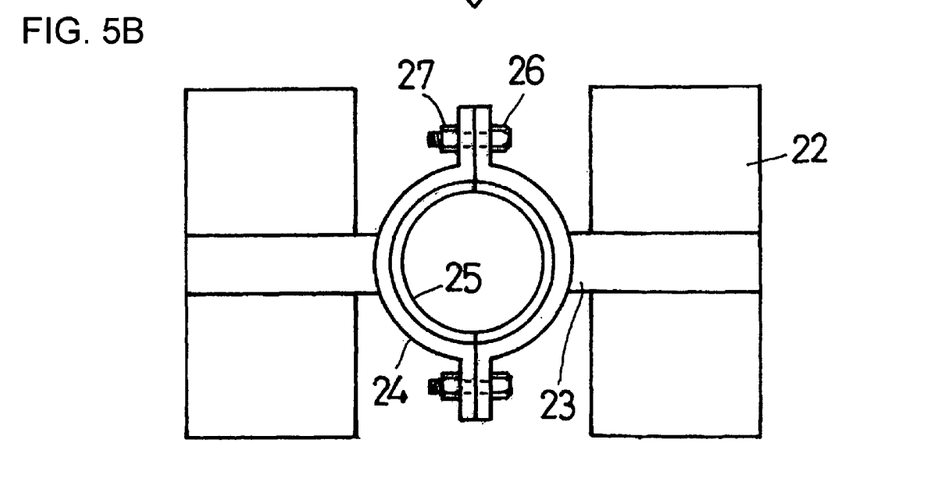

FIGS. 5A and 5B show another example of the holding device 4. In this example, the holding device 4 includes a pair of parts, each of which consists of a plate member 22 and an arm 23 that has a substantially semicircular end 24 and is fixed to the plate member 22. An elastic gasket 25 is attached to the inside of the semicircular end 24. As shown in FIG. 5B, these parts, forming a pair, are attached to the neck or cap of the bottle with bolts 26 and nuts 27. In this example, because the holding device 4 can securely hold the bottle 1 by screwing the bolts 26 into the nuts 27, the holding device 4 can hold the bottle 1 at a portion other than the portion below the bead or cap, where no rib is provided.

Figure 6A:
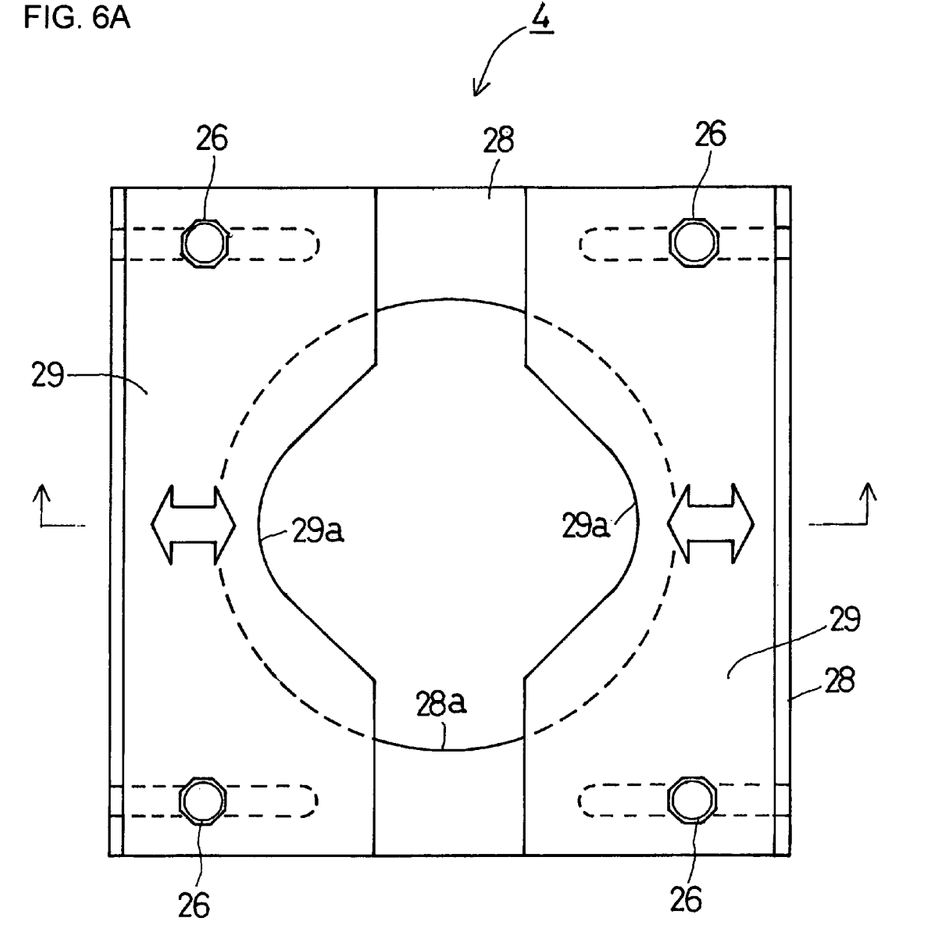
FIGS. 6A and 6B show another example of the holding device.
Figure 6B:
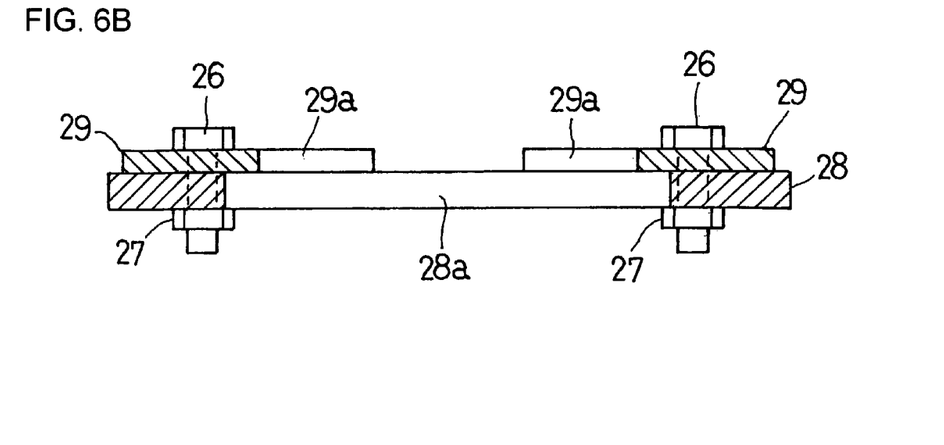

FIGS. 6A and 6B show another example of the holding device 4, showing a plan view and a sectional view, respectively. In this example, the holding device 4 includes a base plate 28 having a hole 28a at the center and two slidable plates 29 each having a mountain-shaped recess 29a at the middle portion of the inner edge. Although the slidable plates 29 are fixed to the base plate 28 with the bolts 26 and the nuts 27, they may be slid in the left-right directions, as indicated by arrows in FIG. 6A, by loosening the bolts 26. After a portion of the bottle to be held is fitted to the recesses 29a, the slidable plates 29 are slid so as to be fitted to that portion and are fixed by the bolts 26. Thus, the bottle 1 is held. This holding device 4 can be used with bottles having various diameters at the portions to be held.

Figure 7:
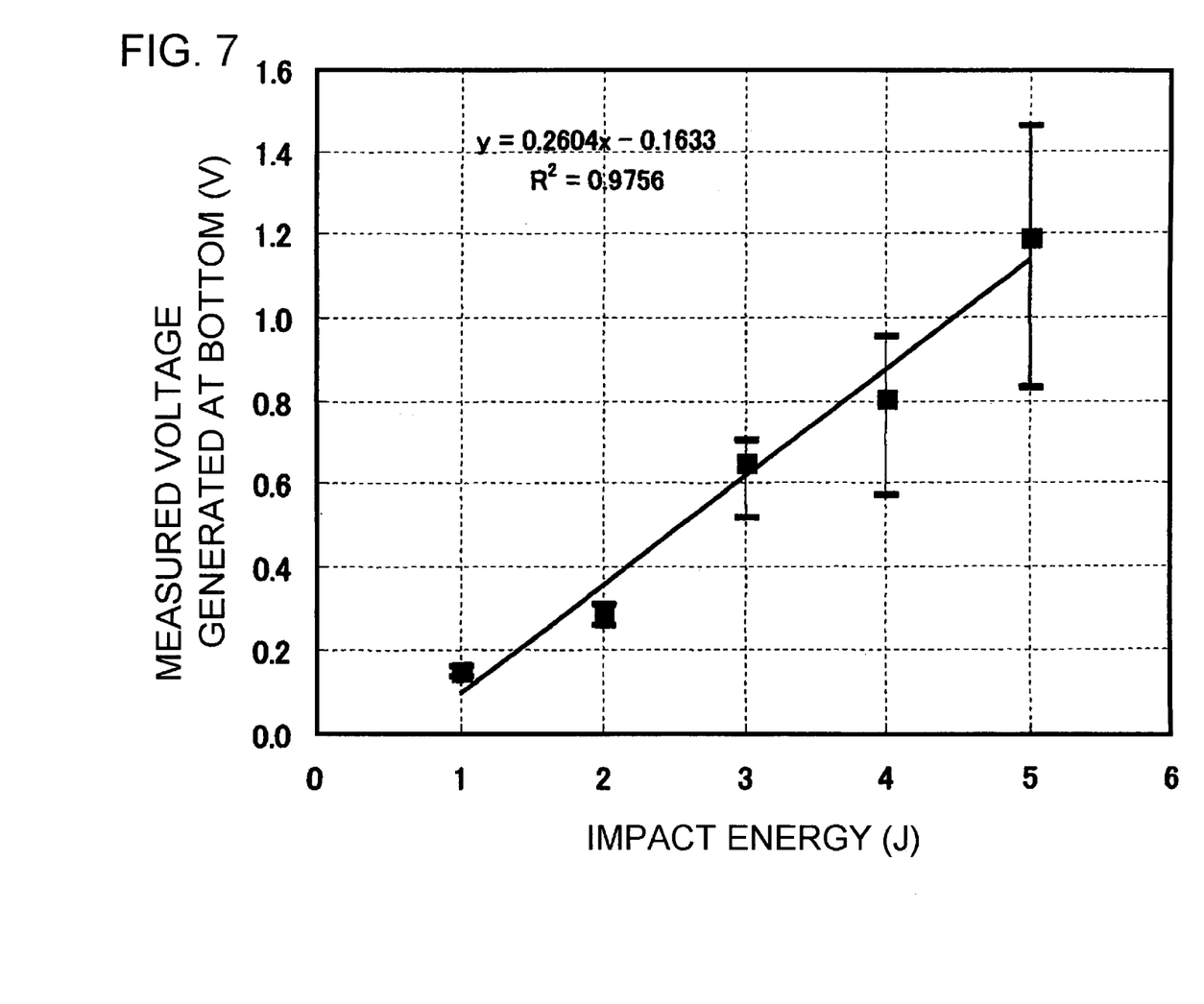
FIG. 7 is a graph showing the relationship between the impact energy and the distortion of the bottom of a bottle in the test method according to the embodiment.

FIG. 7 shows the result of measuring the relationship between the impact energy (drop energy) and the distortion (the amount of deformation) of the bottom surface of the bottle, using the test apparatus shown in FIG. 1. The measurement was performed by dropping the weight on the bottle. A distortion sensor was attached to the center of the outer surface of the bottom thereof. In the test, a commercially available bottle with a capacity of 110 ml (filled with a beverage and fitted with a metal cap) and four soft gel-like cushion materials having a size of 1.5 cm×1.5 cm×1 cm and mainly composed of silicone (JIS K 2207, with a penetration of 55 and a Young's modulus of 119.5 kPa) were used.

In FIG. 7, the ordinate shows the voltage measured by the sensor representing the distortion caused by the water hammer effect of the content occurring when the weight is dropped. The voltage corresponds to the amount of distortion of the bottom surface of the bottle. The abscissa shows the impact energy (=drop energy mgh). The measurement was performed with impact energies from 1 J to 5 J, with an increment of 1 J, and five tests were performed for each impact energy. In FIG. 7, filled squares indicate the averages, and short horizontal lines above and below the filled squares indicate the ranges of variations. As shown in FIG. 7, with the method of the present invention, the impact energy (drop energy) caused by dropping the weight has a strong correlation to (is substantially directly proportional to) the distortion of the bottle. This shows that the impact caused by dropping the weight is assuredly transmitted to the bottle, and the water hammer effect with a significance corresponding to the drop energy of the weight occurs. Accordingly, the water hammer strength can be accurately tested with the method of the present invention.

Figure 8:
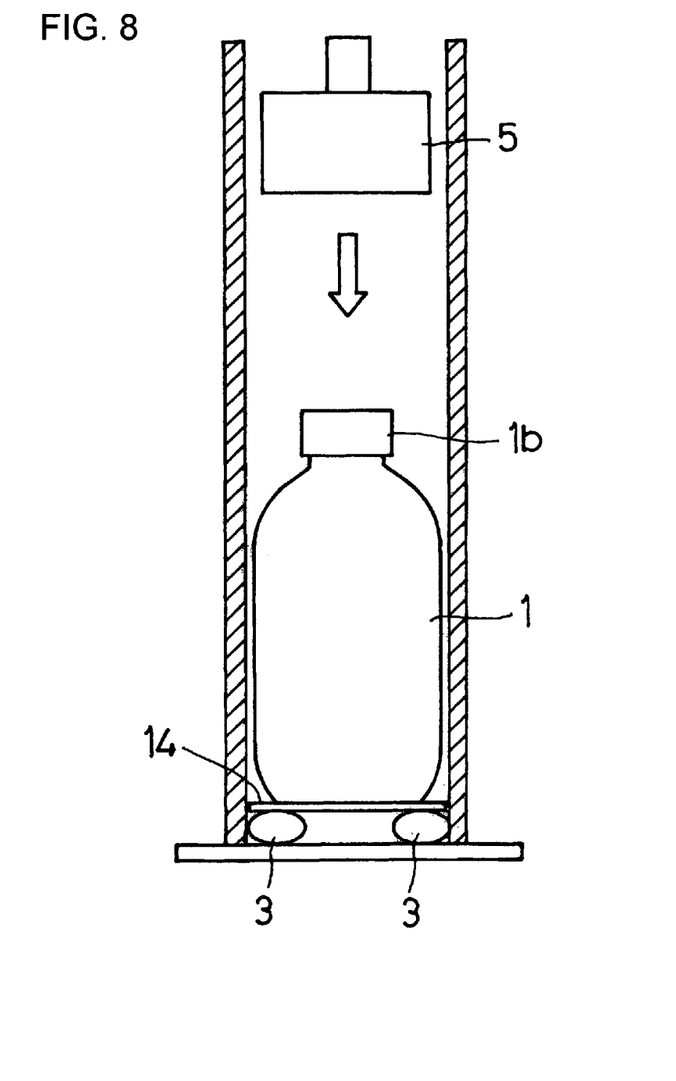
FIG. 8 shows a test method according to a comparison example.
Figure 9:
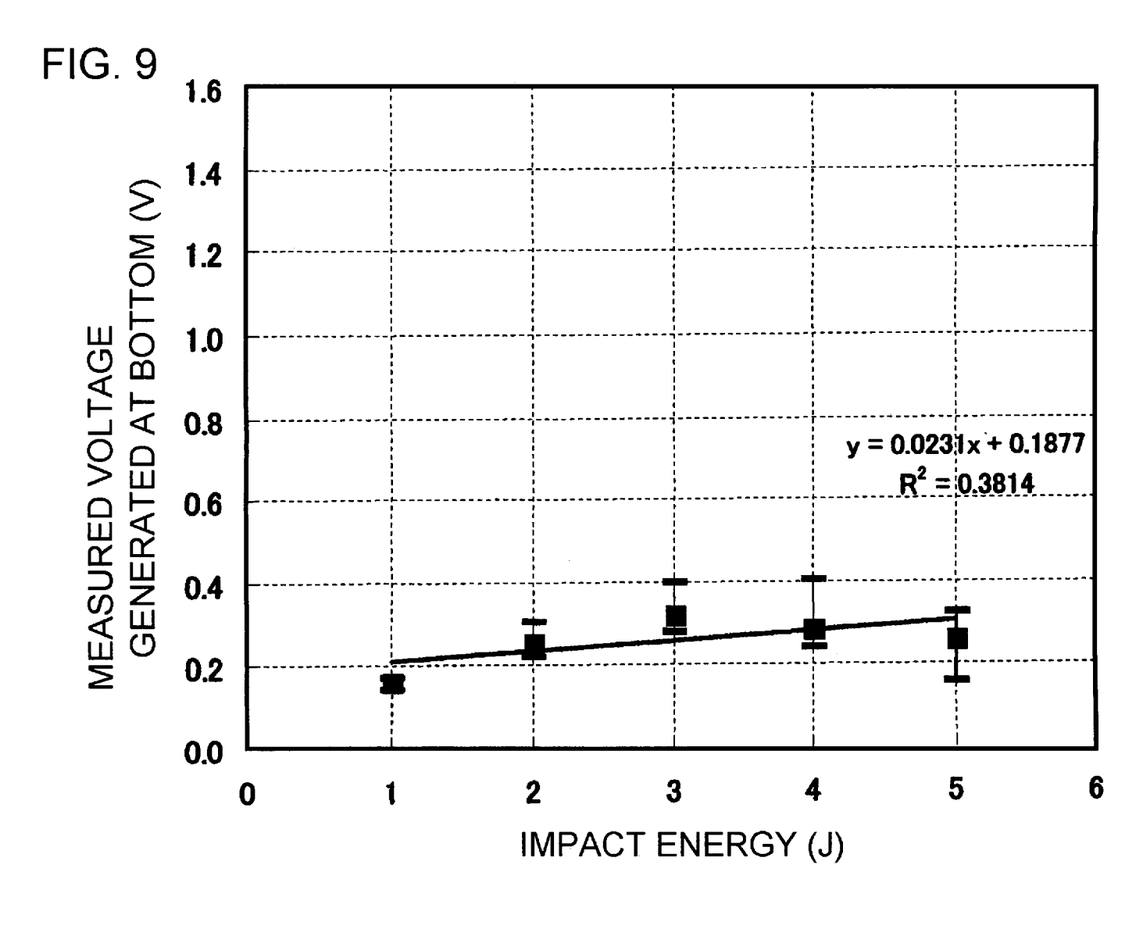
FIG. 9 is a graph showing the relationship between the impact energy and the distortion of the bottom of a bottle in the test method according to the comparison example.

FIG. 8 shows a test method according to a comparison example. The bottle 1 filled with a content and fitted with a cap is placed on a bottom plate 14 placed on the cushion material 3. Then, the weight 5 is dropped thereon. With the test method according to the comparison example shown in FIG. 8, using the same bottle and the cushion materials as those used in the measurement shown in FIG. 7, the relationship between the impact energy (drop energy) and the distortion (the amount of deformation) of the bottom surface of the bottle was measured. The measurement was performed by dropping the weight on the bottle. A distortion sensor was attached to the center of the outer surface of the bottom thereof. The result is shown in FIG. 9. In FIG. 9, filled squares indicate the averages, and short horizontal lines above and below the filled squares indicate the ranges of variations. As shown in FIG. 9, in the comparison example, the average of the amount of distortion of the bottom surface of the bottle is maximum when the impact energy is 3 J and decreases when the impact energy is 4 J or more. This may be because the impact energy caused by dropping the weight is not assuredly transmitted to the bottle because the bottle is inclined due to the impact caused by dropping the weight. Therefore, the water hammer strength cannot be accurately tested with the test method according to the comparison example.

With the method of the present invention, because the weight is dropped on the bottle held at a position above the center of gravity thereof and suspended in the air, the behavior of the bottle subjected to the impact caused by dropping the weight is stable, and the impact energy caused by dropping the weight can be assuredly transmitted to the bottle.

Figure 10:
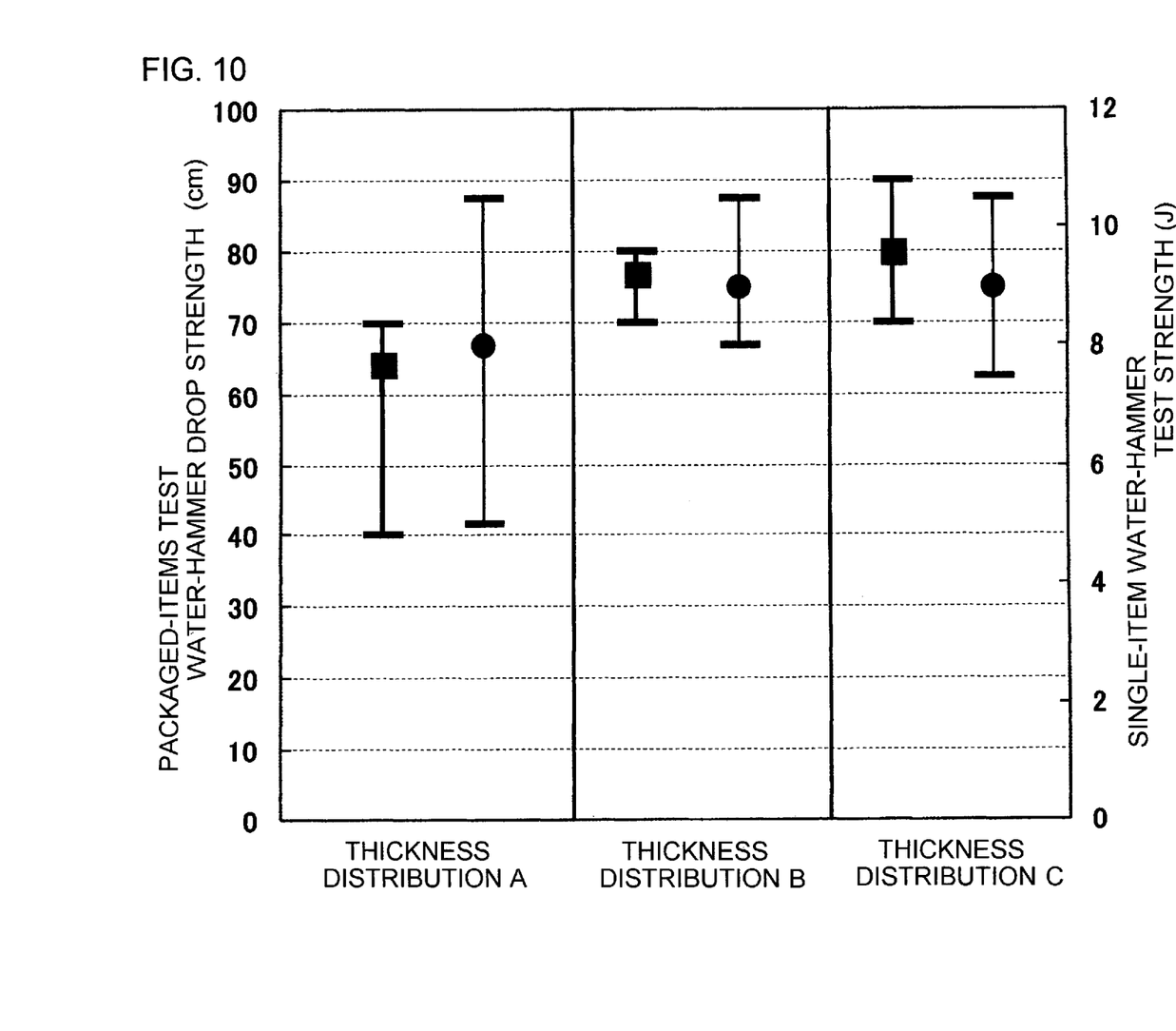
FIG. 10 is a graph showing a comparison between the test method according to the embodiment and a test method for packaged items.

FIG. 10 is a graph showing a comparison between the test results obtained by the method for testing the water hammer strength according to the present invention and the test results obtained by the "water-hammer test method" prescribed by Japan Glass Bottle Association shown in FIG. 11. In the tests, three types of bottles having different thickness distributions (commercially available bottles with a capacity of 110 ml, filled with a beverage and fitted with a metal cap) were used. With the method of the present invention, the test apparatus shown in FIG. 1 and four soft gel-like cushion materials having a size of 1.5 cm×1.5 cm×1 cm and mainly composed of silicone (JIS K 2207, with a penetration of 55 and a Young's modulus of 119.5 kPa) were used. The water hammer strength of bottles having different thickness distributions (thickness distributions A, B, and C) was tested. Ten bottles were tested for each thickness distribution. The test was performed using a weight having a weight of 4.0817 kg. The first drop height was 2.5 cm, and the drop height was increased with an increment of 1.25 cm. The drop energy (mgh) at the time when the bottles were damaged was regarded as the "single-item water-hammer test strength". With the "water-hammer test method" prescribed by Japan Glass Bottle Association, 50 glass bottles packaged in a corrugated cardboard carton were used as samples. For each of the thickness distributions A, B, and C, the water hammer strength of five samples was tested. First, the upper dummies were dropped onto the samples from a drop height of 30 cm. Then, the drop height was increased with an increment of 5 cm (when the drop height was 60 cm or more, the drop height was increased by an increment of 10 cm). The drop height at the time when the sample glass bottles, even one of them, were damaged was regarded as the "packaged-items test water-hammer drop strength". In each of the thickness distributions A, B, and C in FIG. 10, filled squares on the left side indicate the average of the "packaged-items test water-hammer drop strength", and filled circles on the right side indicate the "single-item water-hammer test strength", and short horizontal lines above and below the filled squares and circles indicate the ranges of variations.

As shown in FIG. 10, because the "single-item water-hammer test strength" and the "packaged-items test water-hammer drop strength" substantially correspond to each other, the "packaged-items test water-hammer drop strength" can be estimated by measuring the "single-item water-hammer test strength" and taking into consideration the specifications of the package.

What is claimed is:
1. A method for testing the water hammer strength of a glass bottle, said method comprising:
providing a holding device on a fixing stage with a cushion material located between the holding device and the fixing stage;
providing a bottle filled with a liquid content and fitted with a cap;
holding the bottle with the holding device at a position above the center of gravity of the bottle and suspending the bottle in the air;

dropping a weight directly or indirectly onto the cap to apply an impact to the bottle, the weight being repeatedly dropped while gradually increasing a drop energy of the weight; and determining the water hammer strength of the bottle being tested based on the drop energy of the weight at the time when the bottle is damaged.

2. An apparatus for testing the water hammer strength of a glass bottle, said apparatus comprising:

a fixing stage;

a cushion material placed on the fixing stage;

a holding device placed on said cushion material so that the holding device is supported by the cushion material, the holding device being configured to hold the bottle, at a position above the center of gravity of the bottle and suspend the bottle in the air, the bottle being filled with a liquid content and fitted with a cap; and a weight to be dropped onto the cap to apply an impact to the bottle.

3. The apparatus according to claim 2, further comprising a frame including a base stage and a post standing upright from said base stage, wherein said fixing stage is a plate-like member extending from said post toward one side and having a through-hole configured such that the bottle suspended in the air by said holding device is inserted into said through-hole.

4. The apparatus according to claim 3, further comprising a protection plate for covering the cap and having a bottom surface contacting a top surface of the cap, wherein said weight is arranged to be dropped onto said protection plate so that said weight is indirectly dropped onto the cap via said protection plate.

5. The apparatus according to claim 4, wherein said weight includes a shaft and a weight body formed at a lower end of said shaft, and said apparatus further comprising a guide into which said shaft is inserted so that said weight can vertically move along a predetermined path.

6. The apparatus according to claim 3, wherein said weight includes a shaft and a weight body formed at a lower end of said shaft, and said apparatus further comprising a guide into which said shaft is inserted so that said weight can vertically move along a predetermined path.

7. The apparatus according to claim 2, wherein said fixing stage includes a plurality of posts, said posts being arranged such that the bottle suspended in the air by said holding device is surrounded by said posts.

8. The apparatus according to claim 7, further comprising a protection plate for covering the cap and having a bottom surface contacting a top surface of the cap, wherein said weight is arranged to be dropped onto said protection plate so that said weight is indirectly dropped onto the cap via said protection plate.

9. The apparatus according to claim 8, wherein said weight includes a shaft and a weight body formed at a lower end of said shaft, and said apparatus further comprising a guide into which said shaft is inserted so that said weight can vertically move along a predetermined path.

10. The apparatus according to claim 7, wherein said weight includes a shaft and a weight body formed at a lower end of said shaft, and said apparatus further comprising a guide into which said shaft is inserted so that said weight can vertically move along a predetermined path.

11. The apparatus according to claim 2, wherein said fixing stage is a tubular member, said tubular member being configured such that the bottle suspended in the air by said holding device is positioned in said tubular member.

12. The apparatus according to claim 11, further comprising a protection plate for covering the cap and having a bottom surface contacting a top surface of the cap, wherein said weight is arranged to be dropped onto said protection plate so that said weight is indirectly dropped onto the cap via said protection plate.

13. The apparatus according to claim 12, wherein said weight includes a shaft and a weight body formed at a lower end of said shaft, and said apparatus further comprising a guide into which said shaft is inserted so that said weight can vertically move along a predetermined path.

14. The apparatus according to claim 11, wherein said weight includes a shaft and a weight body formed at a lower end of said shaft, and said apparatus further comprising a guide into which said shaft is inserted so that said weight can vertically move along a predetermined path.

15. The apparatus according to claim 2, further comprising a protection plate for covering the cap and having a bottom surface contacting a top surface of the cap, wherein said weight is arranged to be dropped onto said protection plate so that said weight is indirectly dropped onto the cap via said protection plate.

16. The apparatus according to claim 15, wherein said weight includes a shaft and a weight body formed at a lower end of said shaft, and said apparatus further comprising a guide into which said shaft is inserted so that said weight can vertically move along a predetermined path.

17. The apparatus according to claim 2, wherein said weight includes a shaft and a weight body formed at a lower end of said shaft, and said apparatus further comprising a guide into which said shaft is inserted so that said weight can vertically move along a predetermined path.

* * * * *